US00PP33887P2

(12) United States Plant Patent
Ikeda

(10) Patent No.: US PP33,887 P2
(45) Date of Patent: Jan. 18, 2022

(54) SHIITAKE MUSHROOM NAMED 'CHIKUMASSHU CS-2'

(50) Latin Name: ***Lentinus edodes* (Berk) Sing**
Varietal Denomination: Chikumasshu CS-2

(71) Applicant: CHIKUMAKASEI CO., LTD., Chikuma (JP)

(72) Inventor: Tadao Ikeda, Chikuma (JP)

(73) Assignee: CHIKUMAKASEI CO., LTD., Chikuma (JP)

( * ) Notice: Subject to any disclaimer, the term of this patent is extended or adjusted under 35 U.S.C. 154(b) by 0 days.

(21) Appl. No.: 17/023,585

(22) Filed: Sep. 17, 2020

(51) Int. Cl.
*A01H 15/00* (2006.01)

(52) U.S. Cl.
USPC ..... Plt./394

(58) Field of Classification Search
USPC ..... Plt./394
CPC ..... A01H 15/00
See application file for complete search history.

*Primary Examiner* — Keith O. Robinson
(74) *Attorney, Agent, or Firm* — Seckel IP, PLLC

(57) ABSTRACT

A new variety of shiitake mushroom that has a medium density, late growth according to temperature, an overall scaled cap, an average length of time from spawning to fruiting, and high yield at second and third month.

5 Drawing Sheets

Common name: Shiitake mushroom.
Botanical classification: *Lentinus edodes* (Berk) Sing.
Variety denomination: 'Chikumasshu CS-2'.

BACKGROUND OF THE NEW VARIETY

The present invention relates to a new and distinct variety of Shiitake mushroom, *Lentinus edodes* (Berk) Sing, which has been given the variety denomination 'Chikumasshu CS-2'.

This new mushroom has a medium density, late growth according to temperature, an overall scaled cap, an average length of time from spawning to fruiting, and high yield at second and third month.

ORIGIN OF THE VARIETY

The parent varieties are 'No. 1603' (mother) (not patented) and 'CS-1' (father) (not patented), respectively.

The mother variety was obtained as follows: a monokaryotic hypha of 'Strain A' (an in-house breed) (not patented) was crossed with a monokaryotic hypha of 'Strain C' (a wild variety) (not patented), to obtain a monokaryotic hypha of 'Strain D' (cross-breed) (not patented). Then, a monokaryotic hypha of 'Strain B' (an in-house breed) (not patented) was crossed with the monokaryotic hypha of 'Strain D', to obtain a monokaryotic hypha of 'Strain E' (cross-breed) (not patented). Then, the monokaryotic hypha of 'Strain E' was crossed with a monokaryotic hypha of 'MoriXR18' (patent status unknown to Applicant), to obtain the mother variety 'No. 1603'.

The father variety was obtained as follows: a monokaryotic hypha of 'Strain A' (an in-house breed) was crossed with a monokaryotic hypha of 'Strain C' (a wild variety), to obtain a monokaryotic hypha of 'Strain D' (cross-breed). Then, the monokaryotic hypha of 'Strain D' was crossed with a monokaryotic hypha of 'MoriXR18', to obtain the father variety 'CS1'.

In January 2012, we cross-bred 'No. 1603' with 'CS-1' and grew the new variety. We made a first selection between February and June 2012 and a second selection between June 2012 and January 2013. The characteristics of the new variety were studied from January 2013 to July 2014, and stability was determined from this study. Afterwards, we reproduced the variety by vegetative reproduction through mycelium culture, and the new variety was found to be stable. The claimed plant was asexually reproduced.

The variety was developed and propagated at the air-conditioned facility of Chikumakasei Co., Ltd in Chikuma-shi, Nagano, Japan. The logs were kept at the facility of Sendai-shi, Miyagi, Japan.

Suitable times of spawning and harvesting are as follows:
Spawning: from the end of May.
Harvesting: from the end of June to the end of November.

Cultivation of the variety does not require particular microorganism or chemical treatments or tissue culture.

The variety is currently intended for food production.

SUMMARY OF THE VARIETY

The variety is distinguished by a medium density, late growth according to temperature, an overall scaled cap, an average length of time from spawning to fruiting, and high yield at second and third month, especially as compared to the yields of varieties 'XR-18' and 'KK-S055', which are otherwise relatively similar in cultivation.

A comparison with the varieties 'XR-18' and 'KK-S055' is as follows:

| | 'Chikumasshu CS-2' | 'XR-18' (patent status unknown to Applicant) | 'KX-S055' (patent status unknown to Applicant) |
|---|---|---|---|
| Aerial hyphae | Few | Medium | Many |
| Density of hyphae | Medium | Dense | Dense |
| Temperature of | | | |

-continued

| | 'Chikumasshu CS-2' | 'XR-18' (patent status unknown to Applicant) | 'KX-S055' (patent status unknown to Applicant) |
|---|---|---|---|
| mycelial growths | | | |
| 5° C. | Slow (about 0.2 mm/day) | n/a | Medium (about 0.5 to 0.7 mm/day) |
| 10° C. | Slow (about 0.2 mm/day) | n/a | Medium (about 0.5 to 0.7 mm/day) |
| 15° C. | Slow (about 0.2 mm/day) | n/a | Medium (about 0.5 to 0.7 mm/day) |
| 30° C. | Slow (about 0.2 mm/day) | Medium (about 0.5 to 0.7 mm/day) | Fast (about 0.9 mm/day) |
| Shape in vertical cross-section | Convex top surface | Flat top surface | n/a |
| Flesh type | Flat bottom surface | Flat bottom surface | n/a |
| Hardness of cap | Medium | Hard | n/a |
| Arrangement of scales on cap | Overall | Circum-ference | Circumference |
| Shape of hymenophore | Wavy | n/a | Straight |
| Arrangement of hymenophore | Wavy | n/a | Orderly |
| Width of hymenophore | Very narrow (below about 4 mm) | n/a | Narrow (about 4 to 5 mm) |
| Shape of stipe | Bulbous base | Straight | Straight |
| Ratio cap diameter/stipe thickness | Very large (above about 5.6) | Large | n/a |
| Number of days from spawning to fruiting | About 100-110 days (e.g. 109 days) | About 79 days | About 149 days |
| Average weight for 1 g dry weight fruitbody | About 1.5-2 g (e.g. 1.8 g) | About 2.5 g | n/a |
| Ratio of yield per month | | | |
| 2nd month | About 20-30% (e.g. 23.3%) | n/a | About 10-20% (e.g. 13.4%) |
| 3rd month | About 10-20% (e.g. 14.5%) | n/a | About 0-10% (e.g. 7.7%) |

(n/a: not available)

BRIEF DESCRIPTION OF THE DRAWINGS

In the accompanying drawings, which are as nearly true as is reasonable possible to make in a color illustration of this type.

Figure 1:
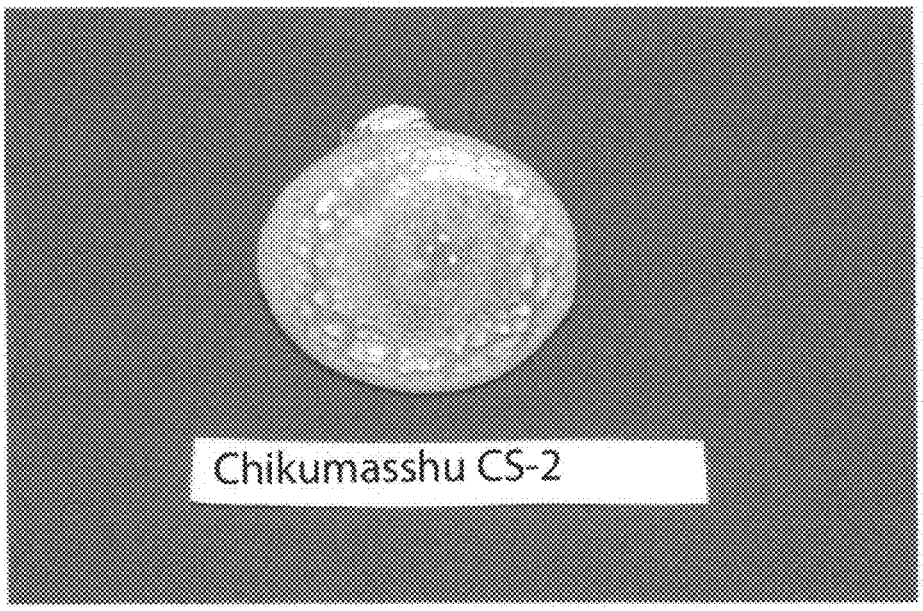
FIG. 1 is a color photograph showing a top surface of a fruiting body of 'Chikumasshu CS-2'.
Figure 2:
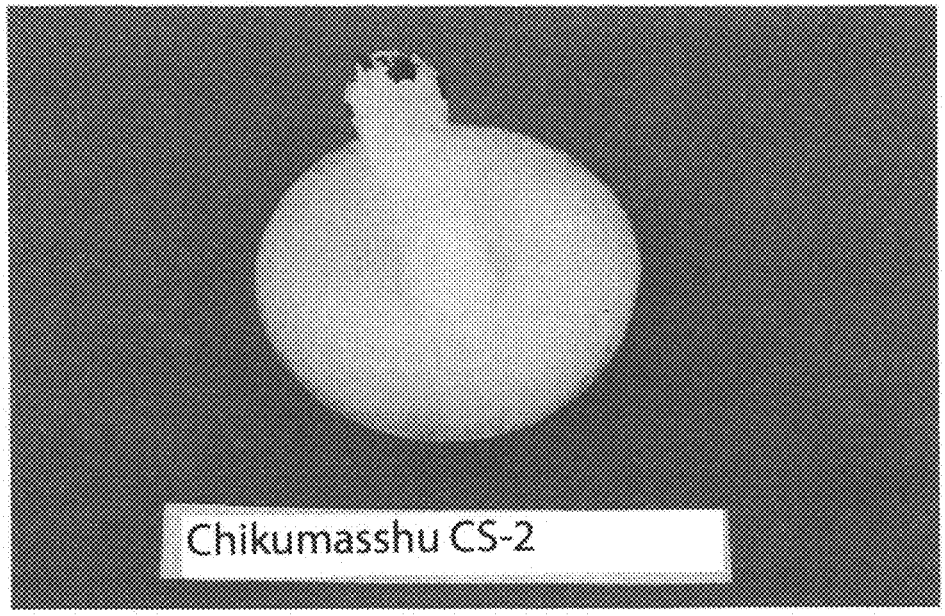
FIG. 2 is a color photograph showing a bottom surface and stem of a fruiting body of 'Chikumasshu CS-2'.
Figure 3:
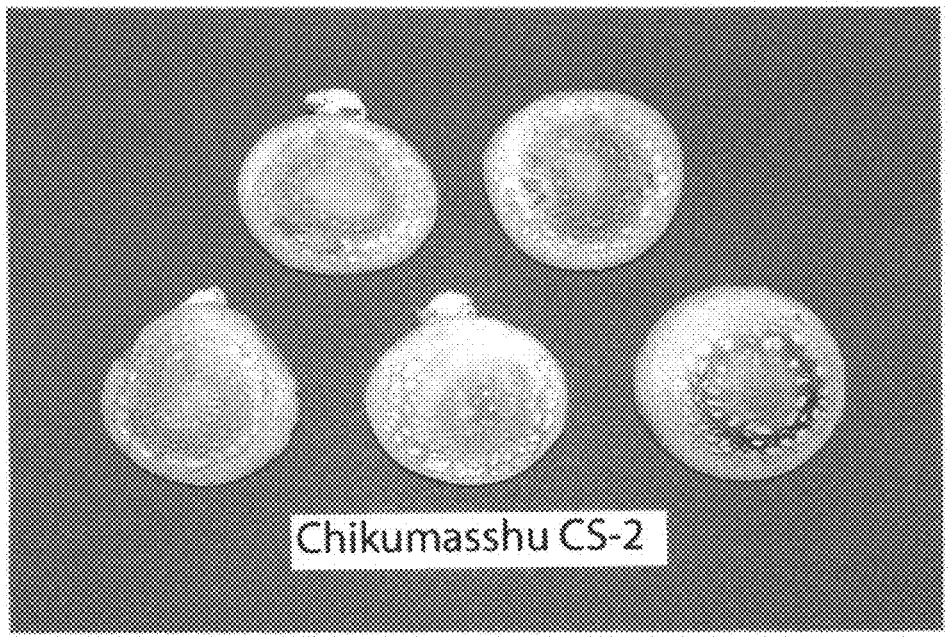
FIG. 3 is a color photograph showing top surfaces of a group of five fruiting bodies of 'Chikumasshu CS-2'.
Figure 4:
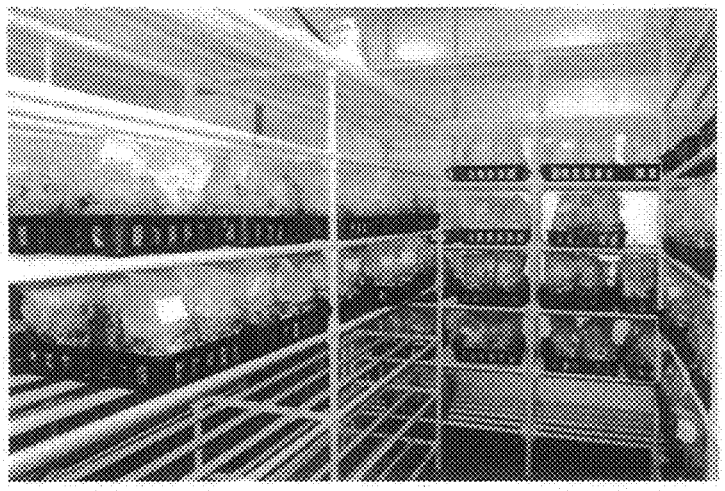
FIG. 4 is a color photograph showing culturing beds of 'Chikumasshu CS-2'.
Figure 5:
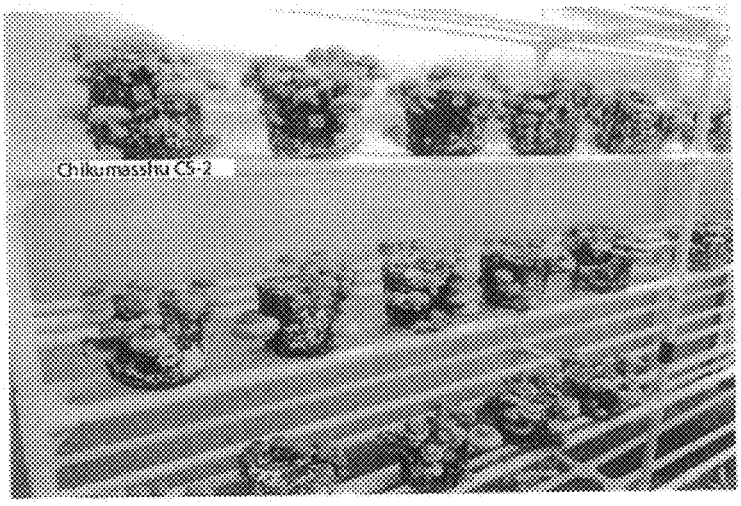
FIG. 5 is a color photograph showing fruiting bodies on culturing beds of 'Chikumasshu CS-2'.
Figure 6:
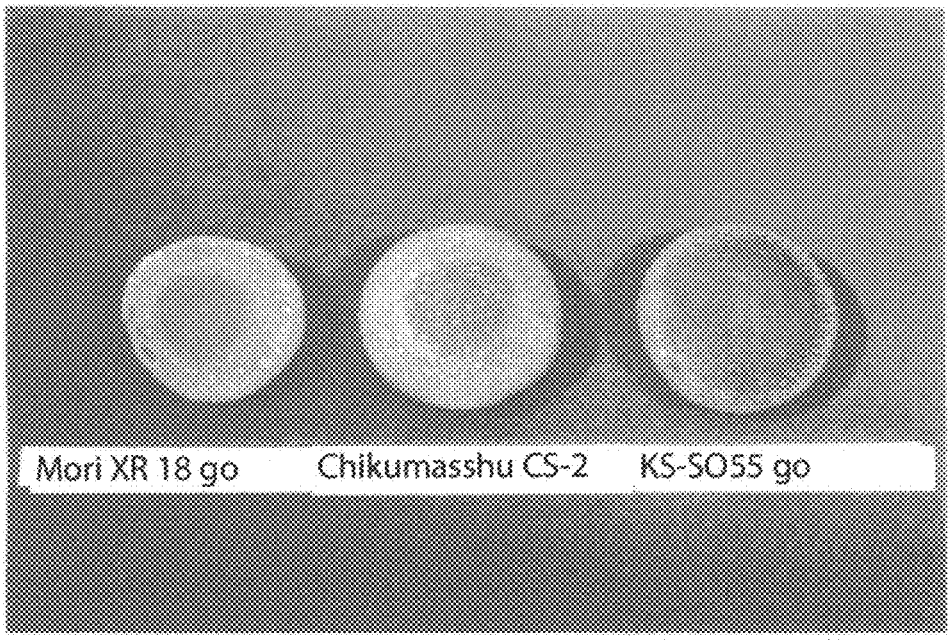
FIG. 6 is a color photographs showing top surfaces of fruiting bodies of 'XR18', 'Chikumasshu CS-2' and 'KX-S055', respectively, for comparison.
Figure 7:
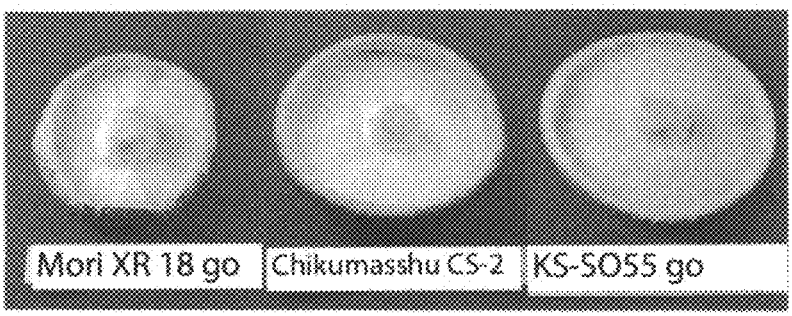
FIG. 7 is a color photographs showing bottom surfaces and stems of fruiting bodies of 'XR18', 'Chikumasshu CS-2' and 'KX-S055', respectively, for comparison.
Figure 8:
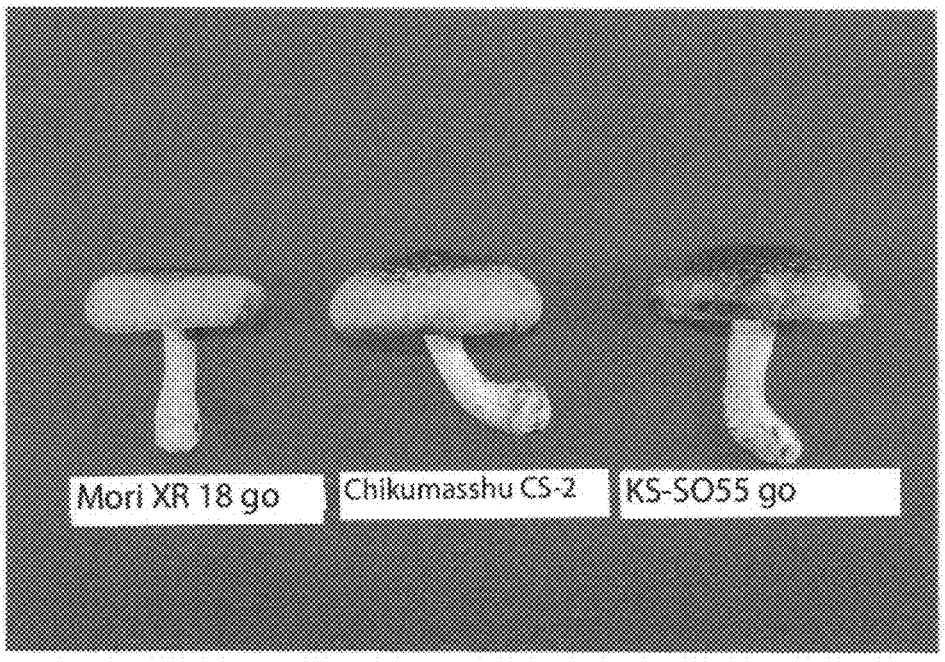
FIG. 8 is a color photographs showing side views of fruiting bodies with stems of 'XR18', 'Chikumasshu CS-2' and 'KX-S055', respectively, for comparison.
Figure 9:
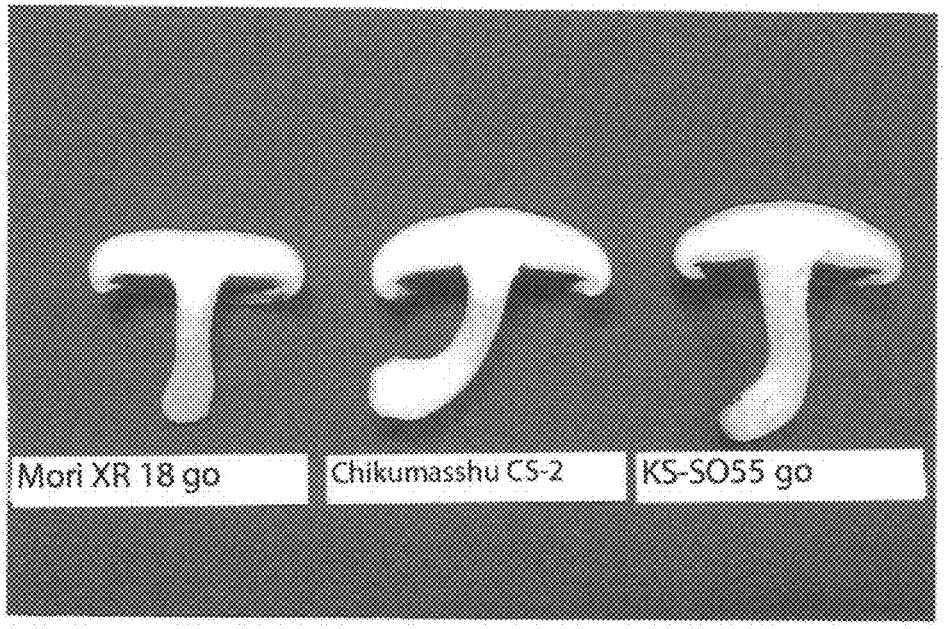
FIG. 9 is a color photographs showing side views in cross-section of fruiting bodies with stems of 'XR18', 'Chikumasshu CS-2' and 'KX-S055', respectively, for comparison.

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'Chikumasshu CS-2' plants within a month of age (and the same for the comparative plants XR18 and KX-S055). The plants were grown between July 2013 and July 2014 in our facilities at 1400-1, Senbonyanagi, Chikuma-shi, Nagano, Japan, and at 7, Aza Naraibansan, Shimoayashi, Aoba-ku, Sendai-shi, Miyagi, Japan.

Colors are given according to The R.H.S. Color Chart, Sixth Edition (2015).

Botanical description:

*Antagonistic reaction*.—Present (aversion line on sawdust medium or PDA).

*Tunic of hyphae*.—Present.

*Aerial hyphae*.—Few.

*Density of hyphae*.—Medium.

*Color of hyphae*.—Colorless.

*Optimum temperature for mycelial growth*.—27° C.

*Temperature of mycelial growth*.—5° C. Slow (about 0.2 mm). 10° C. Slow (about 0.2 mm). 15° C. Slow (about 0.2 mm). 20° C. Slow (about 0.2 mm). 25° C. Slow (about 0.2 mm). 30° C. Slow (about 0.2 mm).

*Shape of top view*.—Round.

*Shape of vertical cross-section*.—Convex top surface.

*Flesh type*.—Flat bottom surface.

*Diameter of cap* (*natural cultivation*).—Medium (about 70 to 80 mm).

*Diameter of cap* (*unfavorable conditions*).—Medium (about 55 to 66 mm) (unfavorable places and periods of cultivation).

*Color of cap top view*.—Yellowish brown (RHS 172A).

*Thickness of cap* (*natural cultivation*).—Medium (about 13 to 16 mm).

*Thickness of cap* (*unfavorable conditions*).—Medium (about 12 to 15 mm) (unfavorable places and periods of cultivation).

*Hardness of cap*.—Medium.

*Arrangement of scales on cap*.—Overall.

*Size of scales*.—Medium (about 59-63 mm).

*Color of scales*.—Yellowish-brown (RHS 172A).

*Gills in cap*.—Present.

*Arrangement of gills*.—Ripple.

*Shape of hymenophore*.—Wavy.

*Arrangement of hymenophore*.—Wavy.

*Width of hymenophore*.—Very narrow (below about 4 mm).

*Density of hymenophore*.—Crowded.

*Color of hymenophore*.—Cream (RHS N155A).

*Shape of stipe*.—Bulbous base.

*Length of stipe*.—Medium (about 47 to 54 mm).

*Ratio cap diameter/stipe length*.—Medium to large (about 3.2 to 5.6).

*Thickness of stipe*.—Thin (about 19 to 22 mm).

*Ratio cap diameter/stipe thickness*.—Very large (above about 5.6).

*Color of stipe surface*.—Pale yellow-green (RHS 155A).

*Color of stipe hair*.—Light yellow-brown (RHS 158D).

*Hair*.—Present.

*Hardness of stipe*.—Hard.

*Tinting of stipe*.—Present.

*Number of days from spawning to fruiting*.—About 100-110 days.

*Harvest period after fruiting treatment*.—About 6-8 days.

*Type of fruiting*.—Concentrated.

*Soaking yield*.—Fitness.

*Water temperature*.—Medium (about 15 to 20° C.).

*Method of secondary fruiting*.—Soaking.

*Fruiting temperature*.—Medium (about 15 to 20° C.).

*Adaptability of culture medium*.—Broad-leaf sawdust.

*Ratio of dry weight fruit body*.—About 10-15%.

*Average weight of dry fruit body*.—About 1.5-2 g.

*Yield per* 100 *kg sawdust medium*.—Small (about 3.3 to 4.0 kg).

*Ratio of yield per year*.—$1^{st}$ year: Over 50%. $2^{nd}$ year: About 20-30%. $3^{rd}$ year: About 10-20%. $4^{th}$ year: Under 10%.

I claim:

1. A new and distinct variety of shiitake mushroom as described and illustrated.

* * * * *